United States Patent
Granados et al.

(12)

(10) Patent No.: US 6,203,992 B1
(45) Date of Patent: Mar. 20, 2001

(54) NUCLEIC ACID PRIMERS AND PROBES FOR DETECTING TUMOR CELLS

(75) Inventors: Edward N. Granados, Vernon Hills; Christi Powell Scheffel, Mundelein, both of IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 09/419,212

(22) Filed: Oct. 15, 1999

(51) Int. Cl.$^7$ .............................. C12Q 1/68; C07H 21/04; C12P 19/34
(52) U.S. Cl. .......................... 435/6; 536/24.31; 536/24.3; 536/23.5; 435/91.2
(58) Field of Search ................... 435/6, 91.2; 536/24.31, 536/23.5, 24.3

(56) References Cited

U.S. PATENT DOCUMENTS 5,766,888   6/1998   Sobol et al. ......................... 435/91.2

FOREIGN PATENT DOCUMENTS

WO9914372 * 3/1999 (WO) .

OTHER PUBLICATIONS

Stasiak et al. Nucleic Acids Research. vol. 15, No. 23, 1987, p. 10058.*
Ruud et al. Int. J. Cancer: 80, 119–125 (Jan. 5, 1999).*
Stratagene Catalog 1988.*
"Immunobead RT–PCR:A Sensitive Method for Detection of Circulating Tumor Cells", *Bio Techniques*, 21:100–105 (1997).
Datta, Y. H., et al., "Sensitive Detection of Occult Breast Cancer by the Reverse–Transcriptase Polymerase Chain Reaction", *Journ of Clinical Oncology*, 12(3):475–482 (1994).

* cited by examiner

*Primary Examiner*—Jeffrey Fredman
*Assistant Examiner*—Juliet C Einsmann
(74) *Attorney, Agent, or Firm*—Paul D. Yasger

(57) ABSTRACT

Nucleic acid sequences are provided that are useful as amplification primers and hybridization probes for detecting CK19 target sequence in a test sample. The primers and probes can be employed in amplification based methods for detecting the presence of CK19 sequences in a test sample. The amplification product can be detected with the assistance of microparticle capture techniques.

7 Claims, No Drawings

SEQUENCE LISTING

<160> NUMBER OF SEQ ID NOS: 8

<210> SEQ ID NO 1
<211> LENGTH: 180
<212> TYPE: DNA
<213> ORGANISM: Homo sapiens

<400> SEQUENCE: 1

```
ggcctgggcc ctcccgcgac tacagccact actacacgac catccaggac ctgcgggaca      60
agattcttgg tgccaccatt gagaactcca ggattgtcct gcagatcgac aacgcccgtc     120
tggctgcaga tgacttccga accaagtttg agacggaaca ggctctgcgc atgagcgtgg     180
```

<210> SEQ ID NO 2
<211> LENGTH: 24
<212> TYPE: DNA
<213> ORGANISM: Artificial Sequence
<220> FEATURE:

-continued

```
<223> OTHER INFORMATION: Primer

<400> SEQUENCE: 2
ccgcgactac agccactact acac                                    24

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
gagcctgttc cgtctcaaa                                          19

<210> SEQ ID NO 4
<211> LENGTH: 15
<212> TYPE: DNA
<213> ORGANISM: Artificial Sequence
<220> FEATURE:
<223> OTHER INFORMATION: Probe

<400> SEQUENCE: 4
ccatccagga cctgc                                              15

<210> SEQ ID NO 5
<211> LENGTH: 13
<212> TYPE: DNA
<213> ORGANISM: Artificial Sequence
<220> FEATURE:
<223> OTHER INFORMATION: Probe

<400> SEQUENCE: 5
atcgacaacg ccc                                                13

<210> SEQ ID NO 6
<211> LENGTH: 15
<212> TYPE: DNA
<213> ORGANISM: Artificial Sequence
<220> FEATURE:
<223> OTHER INFORMATION: Probe

<400> SEQUENCE: 6
gcaggtcctg gatgg                                              15

<210> SEQ ID NO 7
<211> LENGTH: 13
<212> TYPE: DNA
<213> ORGANISM: Artificial Sequence
<220> FEATURE:
<223> OTHER INFORMATION: Probe

<400> SEQUENCE: 7
gggcgttgtc gat                                                13

<210> SEQ ID NO 8
<211> LENGTH: 21
<212> TYPE: DNA
<213> ORGANISM: Artificial Sequence
<220> FEATURE:
<223> OTHER INFORMATION: Primer

<400> SEQUENCE: 8
gagcctgttc cgtctcaaac t                                       21
```

NUCLEIC ACID PRIMERS AND PROBES FOR DETECTING TUMOR CELLS

FIELD OF THE INVENTION

The present invention relates to oncology and, in particular, it relates to oligonucleotides for detecting carcinoma in a test sample.

BACKGROUND OF THE INVENTION

Studies have suggested that the presence of epithelial cells in the hematopoietic system indicates the spread of cancer from a localized area to other parts of the body (also known as metastisis). This discovery is important since metastisis is diagnostic of certain stages of cancer, and decisions concerning the proper treatment of a cancer patient are largely dependent upon properly characterizing the stage of the disease. In particular, treatment of patients having localized cancer can be vastly different from treatment of patients in metastatic stages of cancer.

Early efforts to detect the spread of cancer by detecting epithelial cells in the hematopoietic system included immunocytological assay procedures. Unfortunately, these methods are largely inaccurate because antibodies used in these assays, and ostensibly specific for epithelial cells, demonstrate crossreactivity for cells normally found in the hematopoietic system. Hence, "normal hematopoietic cells" are sometimes detected in the absence of metastatic cells and therefore, false positive results can be obtained according to these assay procedures. Additionally, immunocytological assays lack sensitivity and can produce false negative results when low levels of epithelial cells are actually present in the hematopoietic system. Accordingly, early stages of metastatic cancer can be misdiagnosed using immunocytological asays.

With the advent of nucleic acid amplification reactions such as the polymerase chain reaction (PCR), epithelial cells present in the hematopoietic system can be detected at the nucleic acid level instead of at the protein level. Hence, problems associated with crossreactive antibodies are avoided. Additionally, it is well known that nucleic acid amplification reactions are significantly more sensitive than more conventional antibody based assay methods. Amplification based assays for detecting epithelial cells in the blood stream have therefore provided significant advantages over immunocytological assay methods for detecting early stages of metastatic cancer.

PCR based assays employed to detect epithelial cells in the hematopoietic system have been reported in the literature. Most of these assays target a nucleic acid sequence encoding cytokeratin 19 (CK19), a protein found on the surface of epithelial cells. However, psuedogenes (comprising a nucleic acid sequence that closely mimics the gene for CK19) are present in the human genome. Thus, one challenge facing those developing amplification assays to detect a CK19 target sequence is to design assays that amplify and detect a sequence from the CK19 gene but not the closely related pseudogene.

Additionally, it is well known that amplification primer sequences can be selected based upon computer comparisons of closely related sequences. Theoretically, sequences selected in this manner effectively should produce copies of the selected target sequence when employed according to nucleic acid amplification principles. Notwithstanding the theoretical efficacy of sequences selected in the above manner, it is often times true that such sequences do not produce acceptable amounts of amplification product. Unfortunately, this phenomenon is not understood. Accordingly, while primers initially can be screened using computer programs efficacy cannot be adequately determined until such primers are employed in practice.

A further challenge faces those designing PCR assays that use microparticle capture based detection procedures for detecting amplification products. Specifically, amplified target sequences detected with the assistance of microparticles must be sufficiently short so that amplification product captured on the microparticle does not interfere with the capture of additional amplification product. Accordingly, those choosing to detect amplification products with the assistance of a microparticle are faced with an added restriction in terms of selection of a suitable target sequence. In particular, suitable target sequences are constrained to sequences that are relatively short.

There is therefore a need in the art for a method and sequences that can be employed according to nucleic acid amplification principles to detect a CK 19 target sequence using microparticle based detection techniques.

SUMMARY OF THE INVENTION

The present invention provides nucleic acid sequences that can be used to specifically and sensitively detect a CK 19 target sequence. In particular, primers sequences employed in the present invention are designated SEQ ID NO 2 and SEQ ID NO 3. Sequences identified herein as SEQ ID NO 4, SEQ ID NO 5, SEQ ID NO 6, and SEQ ID NO 7, SEQ ID NO 10, are employed as probes for detecting the amplification product produced by SEQ. ID. NOs. 2 and 3. Combinations of the above sequences can be provided in kits along with other reagents for performing an amplification reaction to detect a CK 19 target sequence in peripheral blood.

The CK 19 target sequence, designated herein as SEQ. ID. NO. 1, can be amplified by forming a reaction mixture comprising nucleic acid amplification reagents, a test sample containing a CK 19 target sequence, and a primer set containing SEQ ID NOs. 2 and 3. Following amplification, the amplified target sequence can be detected. For example, any probe or any combination of the probes designated SEQ ID NOs. 4, 5, 6, and 7 can be employed to hybridize to the amplified target sequence to form a probe/amplification product hybrid which can then be detected using microparticle capture techniques. Hence, the primers or probes can be labeled to capture and detect the amplified target sequence and therefore indicate the presence of the target sequence in the test sample.

DETAILED DESCRIPTION OF THE INVENTION

As previously mentioned, the present invention provides reagents, methods, and kits for amplifying and detecting a CK-19 target sequence in a test sample. In particular, SEQ. ID. Nos. 2 and 3 can be employed as amplification primers to amplify the CK 19 target sequence designated herein as SEQ. ID. NO. 1. It was discovered that these primers specifically and sensitively produce an amplification product that is amenable to microparticle capture and detection techniques. Probe sequences, having SEQ. ID. Nos. 4 through 7 can be employed to insure specificity and detect the amplification product.

The primer and probe sequences disclosed herein, may comprise deoxyribonucleic acid (DNA), ribonucleic acid (RNA) or nucleic acid analogs such as uncharged nucleic acid analogs including but not limited to peptide nucleic acids (PNAs) which are disclosed in International Patent Application WO 92/20702 or morpholino analogs which are described in U.S. Pat. Nos. 5,185,444, 5,034,506, and 5,142,047 all of which are herein incorporated by reference. Such sequences can routinely be synthesized using a variety of techniques currently available. For example, a sequence of DNA can be synthesized using conventional nucleotide phosphoramidite chemistry and the instruments available from Applied Biosystems, Inc, (Foster City, Calif.); DuPont, (Wilmington, Del.); or Milligen, (Bedford, Mass.). Similarly, and when desirable, the sequences can be labeled using methodologies well known in the art such as described in U.S. Pat. Nos. 5,464,746; 5,424,414; and 4,948,882 all of which are herein incorporated by reference. It will be understood, however, that the sequences employed as primers should at least comprise DNA at the 3' end of the sequence and preferably are completely comprised of DNA.

A "target sequence" as used herein means a nucleic acid sequence that is detected, amplified, both amplified and detected or otherwise is complementary to one of the sequences herein provided. While the term target sequence is sometimes referred to as single stranded, those skilled in the art will recognize that the target sequence may actually be double stranded.

The term "test sample" as used herein, means anything suspected of containing the target sequence. The test sample can be derived from any biological source, such as for example, blood, bronchial alveolar lavage, saliva, throat swabs, ocular lens fluid, cerebral spinal fluid, sweat, sputa, urine, milk, ascites fluid, mucous, synovial fluid, peritoneal fluid, amniotic fluid, tissues such as heart tissue and the like, or fermentation broths, cell cultures, chemical reaction mixtures and the like. The test sample can be used (i) directly as obtained from the source or (ii) following a pre-treatment to modify the character of the sample. Thus, the test sample can be pre-treated prior to use by, for example, preparing plasma from blood, disrupting cells, preparing liquids from solid materials, diluting viscous fluids, filtering liquids, distilling liquids, concentrating liquids, inactivating interfering components, adding reagents, purifying nucleic acids, and the like. Most typically, the test sample will be peripheral blood.

SEQ. ID. NOs. 2 and 3 can be used as amplification primers according to amplification procedures well known in the art to amplify the target sequence. Preferably, the sequences provided herein are employed according to the principles of the polymerase chain reaction (PCR) described in U.S. Pat. Nos. 4,683,195 and 4,683,202 which are herein incorporated by reference. It will be understood by those skilled in the art that in the event that the target sequence is RNA, a reverse transcription step should be included in the amplification of the target sequence. Enzymes having reverse transcriptase activity, such as Rt TH, are well known for activity capable of synthesizing a DNA sequence from an RNA template. Reverse transcription PCR (RT PCR) is well known in the art and described in U.S. Pat. Nos. 5,310,652 and 5,322,770 which are herein incorporated by reference.

Thus, amplification methods of the present invention generally comprise the steps of (a) forming a reaction mixture comprising nucleic acid amplification reagents, SEQ. ID. NOS. 2 and 3, and a test sample suspected of containing a target sequence; and (b) subjecting the mixture to amplification conditions to generate at least one copy of a nucleic acid sequence complementary to the target sequence. It will be understood that step (b) of the above method can be repeated several times by thermal cycling the reaction mixture as is well known in the art.

As stated above, the reaction mixture comprises "nucleic acid amplification reagents" that include reagents which are well known and may include, but are not limited to, an enzyme having polymerase activity (and, as necessary, reverse transcriptase activity), enzyme cofactors such as magnesium or manganese; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

"Amplification conditions" are defined generally as conditions which promote hybridizing or annealing of primer sequences to a target sequence and subsequent extension of the primer sequences. It is well known in the art that such annealing is dependent in a rather predictable manner on several parameters, including temperature, ionic strength, sequence length, complementarity, and G:C content of the sequences. For example, lowering the temperature in the environment of complementary nucleic acid sequences promotes annealing. For any given set of sequences, melt temperature, or Tm, can be estimated by any of several known methods. Typically, diagnostic applications utilize hybridization temperatures which are close to (i.e. within 10° C.) the melt temperature. Ionic strength or "salt" concentration also impacts the melt temperature, since small cations tend to stabilize the formation of duplexes by negating the negative charge on the phosphodiester backbone. Typical salt concentrations depend on the nature and valency of the cation but are readily understood by those skilled in the art. Similarly, high G:C content and increased sequence length are also known to stabilize duplex formation because G:C pairings involve 3 hydrogen bonds where A:T pairs have just two, and because longer sequences have more hydrogen bonds holding the sequences together. Thus, a high G:C content and longer sequence lengths impact the hybridization conditions by elevating the melt temperature.

Once sequences are selected for a given diagnostic application, the G:C content and length will be known and can be accounted for in determining precisely what hybridization conditions will encompass. Since ionic strength is typically optimized for enzymatic activity, the only parameter left to vary is the temperature. Generally, the hybridization temperature is selected close to or at the Tm of the primers or probe. Thus, obtaining suitable hybridization conditions for a particular primer, probe, or primer and probe set is well within ordinary skill of one practicing this art.

The amplification product produced as above can be detected during or subsequently to the amplification of the CK-19 target sequence. Methods for detecting the amplification of a target sequence during amplification are described in U.S. Pat. No. 5,210,015 that is herein incorporated by reference. Gel electrophoresis can be employed to detect the products of an amplification reaction after its completion. Preferably, however, amplification products are separated from other reaction components and detected using microparticles and labeled probes. Hence, methods for detecting the amplified CK-19 target sequence include the steps of (a) hybridizing at least one hybridization probe to the nucleic acid sequence complementary to the target sequence, so as to form a hybrid comprising the probe and the nucleic acid sequence complementary to the target sequence; and (b) detecting the hybrid as an indication of the presence of the presence of the target seuquence in the test sample.

Hybrids formed as above can be detected using microparticles and labels that can be used to separate and detect such hybrids. Preferably, detection is performed according to the protocols used by the commercially available Abbott LCx® instrumentation (Abbott Laboratories; Abbott Park, Ill.).

The term "label" as used herein means a molecule or moiety having a property or characteristic which is capable of detection. A label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that directly detectable labels may require additional components such as, for example, substrates, triggering reagents, light, and the like to enable detection of the label. When indirectly detectable labels are used, they are typically used in combination with a "conjugate". A conjugate is typically a specific binding member which has been attached or coupled to a directly detectable label. Coupling chemistries for synthesizing a conjugate are well known in the art and can include, for example, any chemical means and/or physical means that does not destroy the specific binding property of the specific binding member or the detectable property of the label. As used herein, "specific binding member" means a member of a binding pair, i.e., two different molecules where one of the molecules through, for example, chemical or physical means specifically binds to the other molecule. In addition to antigen and antibody specific binding pairs, other specific binding pairs include, but are not intended to be limited to, avidin and biotin; haptens and antibodies specific for haptens; complementary nucleotide sequences; enzyme cofactors or substrates and enzymes; and the like.

A "microparticle", refers to any material which is insoluble, or can be made insoluble by a subsequent reaction and is in a particulate form. Thus, microparticles can be latex, plastic, derivatized plastic, magnetic or non-magnetic metal, glass, silicon or the like. A vast array of microparticle configurations are also well known and include, but are not intended to be limited to, beads, shavings, grains, or other particles, well known to those skilled in the art. Microparticles according to the invention preferably are between 0.1 $\mu$M and 1 $\mu$M in size and more preferably between 0.3 $\mu$M and 0.6 $\mu$M in size.

According to one embodiment, hybrids can be detected by incorporating labels in the primer and/or probe sequences to facilitate detection. Hence, first and second specific binding members attached to the primers and probes can be employed to immobilize the hybrids to microparticles and detect the presence of the microparticles with the assistance of a conjugate.

According to another embodiment, a combination of specific binding members and directly detectable labels can be employed to detect hybrids. For example, specific binding members can be introduced in the hybrids using primers labeled with specific binding members. A directly detectable label can be incorporated into the hybrids using a probe that has been labeled with a directly detectable label. Hence, hybrids can be immobilized to a microparticle using the specific binding member and directly detected by virtue of the label on the probe. It will be understood that other detection configurations are a matter of choice for those skilled in the art.

According to a preferred embodiment, "oligonucleotide hybridization PCR" (variably referred to herein as "OH PCR") amplification reaction as described in U.S. patent application Ser. No. 08/514,704, filed Aug. 14, 1995, that is herein incorporated by reference, is employed to detect the CK19 target sequence. Briefly, the reagents employed in the preferred method comprise at least one amplification primer and at least one internal hybridization probe, as well amplification reagents for performing an amplification reaction.

The primer sequence is employed to prime extension of a copy of a target sequence (or its complement) and is labeled with either a capture label or a detection label. The probe sequence is used to hybridize with the sequence generated by the primer sequence, and typically hybridizes with a sequence that does not include the primer sequence. Similarly to the primer sequence, the probe sequence is also labeled with either a capture label or a detection label with the caveat that when the primer is labeled with a capture label the probe is labeled with a detection label and vice versa. Detection labels have the same definition as "labels" previously defined and "capture labels" are typically used to separate extension products, and probes associated with any such products, from other amplification reactants. Specific binding members (as previously defined) are well suited for this purpose. Also, probes used according to this method are preferably blocked at their 3' ends so that they are not extended under hybridization conditions. Methods for preventing extension of a probe are well known and are a matter of choice for one skilled in the art. Typically, adding a phosphate group to the 3' end of the probe will suffice for purposes of blocking extension of the probe.

According to the above preferred embodiment where the probe initially is part of the reaction mixture, it is preferable to select primers, probes and amplification conditions such that the probe sequence has a lower melt temperature than the primer sequences so that upon placing the reaction mixture under amplification conditions copies of the target sequence or its complement are produced at temperature above the Tm of the probe. After such copies are synthesized, they are denatured and the mixture is cooled to enable the formation of hybrids between the probes and any copies of the target or its complement. The rate of temperature reduction from the denaturation temperature down to a temperature at which the probes will bind to single stranded copies is preferably quite rapid (for example 8 to 15 minutes) and particularly through the temperature range in which an enzyme having polymerase activity is active for primer extension. Such a rapid cooling favors copy sequence/probe hybridization rather that primer/copy sequence hybridization and extension.

The following examples are provided to further illustrate the present invention and not intended to limit the invention.

EXAMPLES

The following examples demonstrate detection of cytokeratin 19 (CK19) using the DNA oligomer primers and probes provided herein. These DNA primers and probes are identified as SEQUENCE ID NO. 2, SEQUENCE ID NO. 3, SEQUENCE ID NO. 4, SEQUENCE ID NO. 5, SEQUENCE ID NO. 6. SEQUENCE ID NO. 7 and SEQUENCE ID NO. 8 and are specific for a region in the CK19 gene. A portion of the CK19 gene target is designated as SEQUENCE ID NO. 1.

In the following examples, SEQUENCE ID NO. 2, SEQUENCE ID NO. 3 and SEQUENCE ID NO. 8 are used as amplification primers specific for the CK19 gene. SEQUENCE ID NO. 4, SEQUENCE ID NO. 5, SEQUENCE ID NO. 6 and SEQUENCE ID NO. 7 are used as internal hybridization probes for the CK19 gene amplification product.

EXAMPLE 1

Preparation of CK19 Primers and Probes

A. CK19 Primers

Target-specific primers and probes were designed to amplify and detect the CK19 gene target sequence by oligonucleotide hybridization PCR. These primers are SEQUENCE ID NO. 2, SEQUENCE ID NO. 3 and SEQUENCE ID NO. 8. Primer sequences were synthesized using standard oligonucleotide synthesis methodology and haptenated with adamantane at their 5' ends using standard cyanoethyl phosphoramidite coupling chemistry as described in U.S. Pat. No. 5,424,414 incorporated herein by reference.

B. CK19 Probes

The detection probes were designed to hybridize with the amplified CK19 target sequence by oligonucleotide hybridization. These probes are SEQUENCE ID NO. 4, SEQUENCE ID NO. 5, SEQUENCE ID NO. 6 and SEQUENCE ID NO. 7. The probe sequences were synthesized using standard oligonucleotide synthesis methodology and haptenated with two carbazoles at the 3' end using standard cyanoethyl phosphoramidite coupling chemistry as described in U.S. Pat. No. 5,464,746 (herein incorporated by reference).

EXAMPLE 2

Preparation of CK19 mRNA and cDNA

CK19 RNA was extracted from the T47D Ductal Carcinoma cell line obtained from American Type Culture Collection, ATCC #HTB-133, Rockville, Md.

RNA was extracted and purified from the T47D cell cultures using the TRIzol® reagent from Gibco, Grand Island, N.Y., following the manufacturer's directions. Purified RNA was quantitated by spectrophotometry using an absorbance reading at 260 nm and an extinction coefficient of 40, or quantitated on a per cell basis.

cDNA was prepared by incubating the purified RNA from 1 to $10 \times 10^6$ cells (prepared above) with 2.5 units MuLV Reverse Transcriptase in a buffer of 10 mM Tris-HCl, pH 8.3, 50 mM KCl, 5 mM $MgCl_2$, containing 1 mM each dGTP, dATP, dCTP and dTTP, 0.5 units of RNase Inhibitor and 2.5 µM Oligo $d(T)_{16}$, at 42° C. for 30 minutes. This was followed by heating at 99° C. for 5 minutes, cooling at 4° C. for 5 minutes and storage at 4° C.

EXAMPLE 3

Detection of CK19

A. Detection of CK19 cDNA

The cDNA from the T47D cell line (prepared as described in Example 2) was diluted to the equivalent of 1 cell in 10 µl in water. The diluted cDNA was then PCR amplified and detected using the SEQ ID NO. 2 and SEQ ID NO. 3 as primers and SEQ ID NO. 4 and SEQ ID NO. 5 as detection probes. All reactions were performed in 190 µl of buffer (pH 8.15) containing 50 mM N,N,-bis[2-Hydroxyethyl] glycine, 81.7 mM potassium acetate, 33.33 mM potassium hydroxide, 0.01 mg/ml bovine serum albumin, 0.1 mM ethylene diaminetetraacetic acid, 0.02 mg/ml sodium azide and 8% (w/v) glycerol. The reaction mixtures used recombinant *Thermus thermophilus* polymerase at a concentration of 5 units/reaction, with dATP, dGTP, dTTP and dCTP at 0.15 mM each. SEQ ID NO. 2 was used at a concentration of 250 nM, SEQ ID NO. 3 was used at a concentration of 500 nM, and both probes were present at 10 nM each.

Manganese chloride was added at a final concentration of 1.63 mM just prior to the addition of the 10 µl sample. Testing was done in replicates of three with water and human placental DNA (Sigma Chemical Co., St. Louis, Mo.) as negative controls.

Reaction mixtures were PCR amplified by cycling at 94° C. for 40 seconds/58° C. for 60 seconds for 45 cycles in a Perkin-Elmer 480 Thermal Cycler. After the reaction mixtures were thermal cycled, the mixtures were maintained at 97° C. for 5 minutes and probe oligo hybridization was accomplished by lowering the temperature to 12° C. for 5 minutes. Following probe hybridization, samples were held at 12° C. before being tested.

Reaction products were detected on the Abbott LCx® system (available from Abbott Laboratories, Abbott Park, Ill.). A suspension of anti-carbazole antibody coated microparticles and an anti-adamantane antibody/alkaline phosphatase conjugate (all of which are commercially available from Abbott Laboratories, Abbott Park, Ill.) were used in conjunction with the LCx® to capture and detect the reaction products. The average values from this experiment (calculated as counts/second/second; c/s/s) and standard deviations (SD) are presented in TABLE 1 and show specific detection of CK19 cDNA from the equivalent of one T47D cell.

TABLE 1

| Sample | Concentration per Reaction | LCx ® rate (c/s/s) | LCx ® rate (SD) |
| --- | --- | --- | --- |
| T47D cDNA | 1 cell | 907 | 18.17 |
| human placental DNA | 100 ng | 27 | 0.29 |
| Water | 0 | 14 | 1.21 |

Additionally, just after the thermal cycling step above, a small amount of sample was removed prior to oligo hybridization and was visualized on a 2% agarose gel stained with SYBR® Green. The gel showed the expected 152 base pair product (data not shown).

B. Sensitivity of detection of CK19 from RNA or cDNA

The purified RNA from the T47D cell line, prepared as described in Example 2., was diluted 10-fold in water from $1 \times 10^4$ to $1 \times 10^{-4}$ cells per reaction, then reverse transcribed using the reaction mixture as described above in Example 3.A., with an initial incubation at 60° C. for 30 minutes. Samples were then PCR amplified and detected as in Example 3.A. Testing was done in triplicate using water as a negative control.

This was compared to using the cDNA from the T47D cell line as the starting material, with cDNA prepared as described in Example 2., and diluted 10-fold in water from $1 \times 10^3$ to $1 \times 10^{-4}$ cells per reaction. Reaction mixtures were PCR amplified and detected as described above in Example 3.A.

The average values from this experiment (calculated as counts/second/second; c/s/s) and standard deviations (SD) are presented in TABLE 2 and show detection of CK19 from T47D cells at concentrations as low as $1 \times 10^{-4}$ cells per reaction with RNA as the starting sample, and $1 \times 10^{-3}$ cells per reaction with cDNA as the starting sample. Thus this method, with these primers and probes, is capable of detecting CK19 from a starting sample of either RNA or cDNA, which could be important in a clinical laboratory setting since cDNA may be prepared well ahead of time, stored more easily, and is more stable, with less risk of degradation.

TABLE 2

| Sample (cells/reaction) | RNA LCx ® rate c/s/s (SD) | cDNA LCx ® rate c/s/s (SD) |
|---|---|---|
| $1 \times 10^4$ | 1215 (34) | ND |
| $1 \times 10^3$ | 1176 (37) | 1177 (34) |
| $1 \times 10^2$ | 1132 (22) | 1199 (43) |
| $1 \times 10^1$ | 1122 (24) | 1119 (22) |
| $1 \times 10^0$ | 1114 (45) | 1135 (29) |
| $1 \times 10^{-1}$ | 1139 (18) | 1143 (10) |
| $1 \times 10^{-2}$ | 1050 (47) | 1134 (40) |
| $1 \times 10^{-3}$ | 805 (105) | 949 (183) |
| $1 \times 10^{-4}$ | 946 (73) | 21 (1.0)* |
| Water | 20 (0.5) | 21 (1.6) |

*one aberrant value deleted

EXAMPLE 4

Detection of CK19 with One vs. Two Probes

Purified T47D cDNA, prepared as in Example 2., was diluted to 0.025 cells/reaction in water, then PCR amplified in triplicate and detected using both SEQ ID NO. 4 and SEQ ID NO. 5 detection probes as in Example 3.A. or using only SEQ ID NO. 5 as the sole detection probe. Water and human placental DNA were used as negative controls.

The average values from this experiment (calculated as counts/second/second; c/s/s) and standard deviations (SD)) are shown in Table 3 and indicate that use of both probes results in an increased signal without increasing the background of the assay. Thus using both probes instead of just one probe is an advantage in the detection of CK19.

TABLE 3

| Sample | Concentration per Reaction | Single Probe LCx ® rate c/s/s (SD) | Both Probes LCx ® rate (SD) |
|---|---|---|---|
| T47D cDNA | 0.025 cells | 672 (60)* | 955 (65) |
| human placental DNA | 1 ug | 41 (7.4) | 45 (9.0) |
| Water | 0 | 21 (1.7) | 25 (2.9) |

*one aberrant value deleted

EXAMPLE 5

Comparison of Primer Length

A comparison was made between the use of the SEQ ID NO. 3 primer and the SEQ ID NO. 8 primer, which contains 2 extra nucleotides. Purified T47D cDNA, prepared as in Example 2., was diluted to 0.05 cells/reaction in water, then PCR amplified in replicates of six as in Example 3.A. except that the cycling conditions were changed to 45 cycles of 94° C. for 40 seconds/58° C. for 80 seconds. The reaction mixtures were as in Example 3.A. using the SEQ ID NO. 2 primer with either the SEQ ID NO. 3 or SEQ ID NO. 8 primer. Water and human placental DNA were tested in triplicate as negative controls. The reaction products were detected as in Example 3.A.

The data from this experiment is shown in Table 4 and indicates that use of the SEQ ID NO. 8 primer in place of the SEQ ID NO. 3 primer is detrimental to the assay since it results in a higher background with the human placental DNA and therefore a loss of specificity.

TABLE 4

| Sample | Concentration per Reaction | Primer SEQ ID NO. 3 LCx ® rate c/s/s (SD) | Primer SEQ ID NO. 8 LCx ® rate c/s/s (SD) |
|---|---|---|---|
| T47D cDNA | 0.05 cells | 633 (58) | 685 (90) |
| human placental DNA | 1 ug | 52 (8.7) | 403 (41) |
| Water | 0 | 26 (ND) | 26 (6.3) |

While the invention has been described in detail and with reference to specific embodiments, it will be apparent to one skilled in the art that various changes and modifications may be made to such embodiments without departing from the spirit and scope of the invention.

---

What is claimed is:

1. A composition of matter comprising an oligonucleotide which consists of SEQ ID NO: 2 and an oligonucleotide which consists of SEQ ID NO: 3.

2. A composition of matter for detecting a CK19 target sequence comprising an oligonucleotide which consists of SEQ ID NO: 2, an oligonucleotide which consists of SEQ ID NO: 3, and a sequence selected from the group consisting of SEQ ID NO 4, SEQ ID NO 5, SEQ ID NO 6, and SEQ ID NO 7.

3. A method of amplifying a CK19 target sequence comprising the steps of:
   (a) forming a reaction mixture comprising nucleic acid amplification reagents, the composition of matter of claim 1, and a test sample suspected of containing a CK 19 target sequence; and
   (b) subjecting the mixture to amplification conditions to generate at least one copy of a nucleic acid sequence complementary to the target sequence.

4. A method for detecting a CK19 target sequence in a test sample comprising the steps of:
   (a) forming a reaction mixture comprising nucleic acid amplification reagents, the composition of matter of claim 1, and a test sample suspected of containing a target sequence;
   (b) subjecting the mixture to amplification conditions to generate at an amplification product;
   (c) providing a probe selected from the group consisting of SEQ ID NO 4, SEQ ID NO 5, SEQ ID NO 6, and SEQ ID NO 7;
   (d) hybridizing the probe to the amplification product to form a hybrid; and
   (e) detecting the hybrid as an indication of the presence of the CK19 target sequence in the test sample.

5. The method of claim 4 further comprising the step of immobilizing the hybrid to a microparticle before detecting the hybrid.

6. A kit for amplifying a CK19 target sequence comprising:
   (a) an oligonucleotide which consists of SEQ ID NO: 2 and an oligonucleotide which consists of SEQ ID NO: 3; and
   (b) amplification reagents.

7. The kit of claim 6 further comprising a probe selected from the group consisting of SEQ ID NO 4, SEQ ID NO 5, SEQ ID NO 6, and SEQ ID NO 7.

* * * * *